Figure 1:
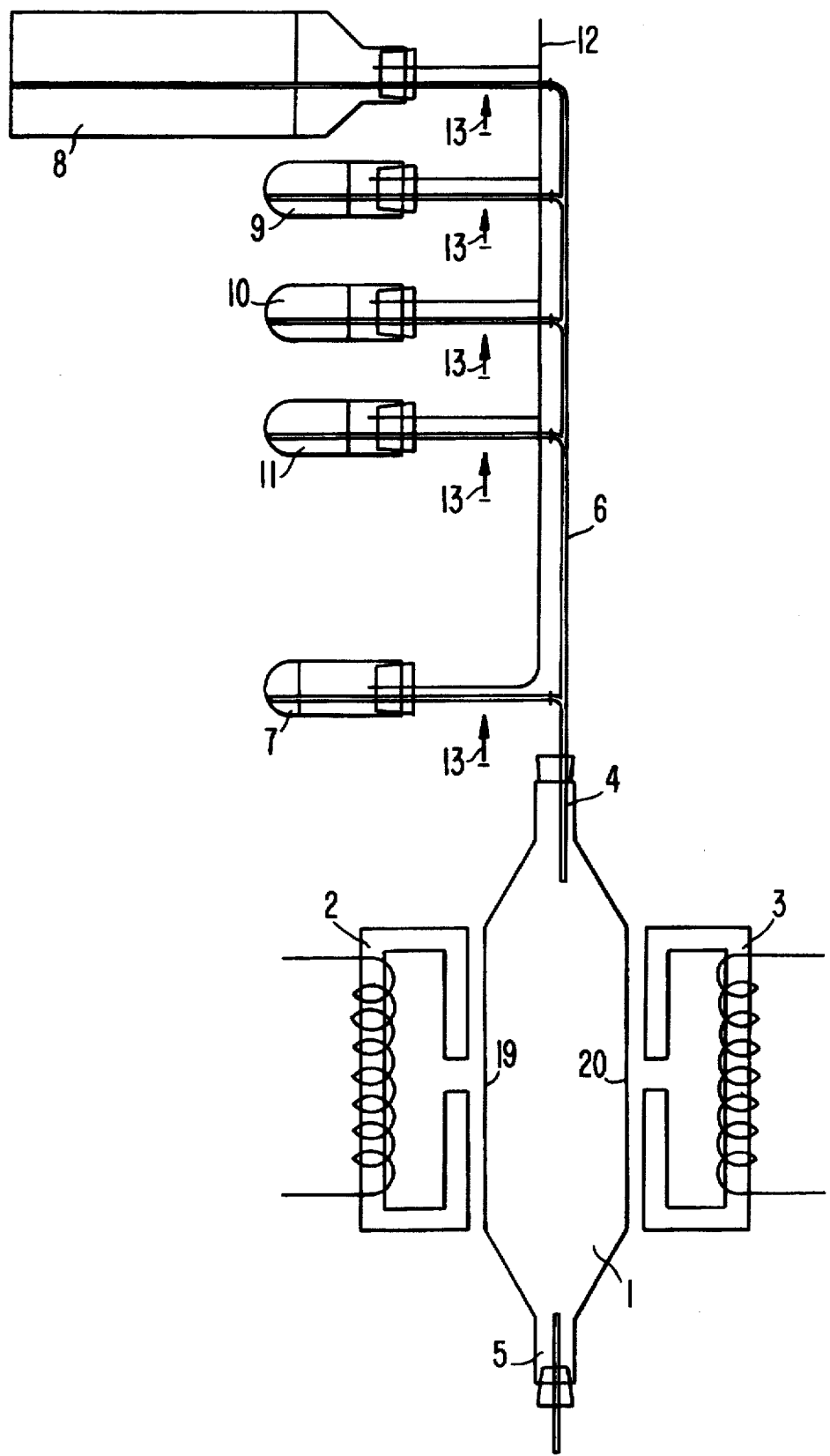

United States Patent [19]
Lea et al.

[11] Patent Number: 5,681,478
[45] Date of Patent: Oct. 28, 1997

[54] METHOD AND APPARATUS FOR MAGNETICALLY SEPARATING AND RESUSPENDING SUPER-PARAMAGNETIC PARTICLES IN A SOLUTION

[75] Inventors: Tor Erling Lea, Oslo; Bjørn Kirkaas Pedersen, Haslum; Harald Kristian Naess, Oslo, all of Norway

[73] Assignee: Diatec Instruments A/S, Oslo, Norway

[21] Appl. No.: 852,182

[22] PCT Filed: Dec. 6, 1990

[86] PCT No.: PCT/EP90/02122

§ 371 Date: Jun. 2, 1992

§ 102(e) Date: Jun. 2, 1992

[87] PCT Pub. No.: WO91/09308

PCT Pub. Date: Jun. 27, 1991

[30] Foreign Application Priority Data

Dec. 7, 1989 [GB] United Kingdom ............... 8927744

[51] Int. Cl.⁶ .................................................. B01D 35/06
[52] U.S. Cl. ............... 210/695; 210/222; 356/36; 356/417
[58] Field of Search .................. 210/222, 695; 366/273; 436/177, 526; 356/36, 417

[56] References Cited

U.S. PATENT DOCUMENTS

| | | | |
|---|---|---|---|
| 2,973,096 | 2/1961 | Greaves | 210/222 |
| 3,219,318 | 11/1965 | Hershler | 366/273 |
| 3,703,958 | 11/1972 | Kolm | 210/695 |
| 3,970,518 | 7/1976 | Giaever | 435/239 |
| 3,985,649 | 10/1976 | Eddelman | 210/695 |
| 4,075,462 | 2/1978 | Rowe | 377/10 |
| 4,297,337 | 10/1981 | Mansfield et al. | 424/1 |
| 4,698,302 | 10/1987 | Whitehead et al. | 435/94 |
| 4,895,650 | 1/1990 | Wang | 210/222 |
| 5,147,529 | 9/1992 | Lee et al. | 210/695 |
| 5,428,451 | 6/1995 | Lea et al. | 356/417 |

FOREIGN PATENT DOCUMENTS

| | | |
|---|---|---|
| 318913 | 6/1989 | European Pat. Off. . |
| 58-193687 | 2/1984 | Japan . |
| 2134819 | 8/1984 | United Kingdom . |
| WO 83/03920 | 11/1983 | WIPO . |
| WO/88/06485 | 9/1988 | WIPO . |
| WO 91/09297 | 6/1991 | WIPO . |

*Primary Examiner*—Matthew O. Savage
*Attorney, Agent, or Firm*—Foley & Lardner

[57] ABSTRACT

Superparamagnetic particles are separated from a suspension thereof in a first fluid and re-suspended in the same or another fluid in a container by subjecting them to a first application of a magnetic field to draw the particles to a surface or zone of the container and subsequently re-suspending the particles in the fluid within the container by a second application of a magnetic field. Apparatus is disclosed including a container (1), electromagnets (2,3) for producing the first and second applications of magnetic fields, reagent receptacles (7), and a wash flask (8). A particle counting device may also provided and such apparatus may be used to count cells.

12 Claims, 2 Drawing Sheets

METHOD AND APPARATUS FOR MAGNETICALLY SEPARATING AND RESUSPENDING SUPER-PARAMAGNETIC PARTICLES IN A SOLUTION

This invention relates to a method and apparatus for separating superparamagnetic particles from a fluid suspension thereof and re-suspending them in the same or another fluid.

It has been proposed, e.g. in EP 106873, and U.S. Pat. No. 3,970,518, to use superparamagnetic particles for the immobilisation or isolation of a wide range of substrates. These may include proteins, nucleic acids, viruses and cells. Such particles have the advantage that they can be readily separated together with the immobilised substrate from a suspension thereof, for example a reaction medium, by application of a magnet to the wall of the vessel containing the suspension whereupon the particles are drawn to the wall as a relatively compact aggregate. The fluid is then readily removed from the vessel and replaced by a second fluid, for example a wash solution or a second reagent whereupon the magnetic field is removed and the aggregated magnetic particles re-suspended by relatively vigorous agitation. On the very small scale, the operator may effect such agitation by flicking the container with his finger but it will be appreciated that this will not be appropriate on the larger scale or in automated systems. It has been suggested that, rather than remove the magnet before re-suspension of the particles it might be possible to rotate the magnet around the container and thereby re-suspended the particles. However, it has been found that rotation of the magnet produces a rolling wave of particles; the particles staying as a compact aggregate but rolling over one another and thus continuing to entrap contaminants and reagents.

There is thus a need for a reliable and readily automated method of re-dispersing superparamagnetic particles after magnetic aggregation. It should be noted that superparamagnetic particles do not retain magnetisation as would be the case with magnetic particles. Thus, when the initial magnetic field is removed, there are no magnetic forces between the particles and the aggregate is held together by compaction.

We have found that by the first application of a magnetic field and, subsequently, a second application of a magnetic field, superparamagnetic particles may be aggregated and efficiently re-suspended without physical agitation. This finding is surprising in view of the fact that rotation of a magnet to change the magnetic field influencing the particle aggregate failed to produce effective re-suspension.

One aspect of our invention provides a method of separating superparamagnetic particles from a suspension thereof in a first fluid and re-suspending said particles in the same or another fluid whereby said suspension in a container is subjected to a first application of a magnetic field to draw said particles to a surface or zone of said container and subsequently said particles are re-suspended in the same or another fluid within said container by a second application of a magnetic field to draw the particles into said fluid.

The invention has the advantages that it leads to rapid and efficient re-suspension of the particles with little clumping and subjects the particles to relatively low shear. The method may be readily repeated several times so that the particles may be washed or treated with one or more reagents. In general, the particles will move across the chamber i.e., in a direction towards a central interior space of the chamber that is inwardly spaced from the peripheral interior surface of a container defining the chamber, at a speed related to the magnetic field and will thus comprise a moving suspension which contacts the fluid in the chamber particularly efficiently.

It will be clear to a person skilled in the art that the first and second applications of magnetic fields may be produced by the same magnet; the magnet being removed from close proximity to the container so that its magnetic field has little or no effect on the particles, and then being returned to the container at a different location such that it provides the second application of a magnetic field for re-suspension of the particles. Conversely, the magnet may, if an electromagnet, be energised to effect aggregation, de-energised and then re-energised at a different position relative to the container either by moving the latter or the electromagnet.

However, it is desirable to avoid unnecessary moving parts, especially in automated systems, so we prefer to use two spaced electromagnets to generate the first and second magnetic fields. Use of electromagnets has the additional advantage that the strengths of the magnetic fields can be varied with respect to time while they are being applied. Thus, for example, an initially strong second magnetic field may be applied to re-suspend the particles and the strength of the field can then be reduced with time to avoid unnecessarily firm aggregation on the opposite wall of the container. In the case of successive aggregations and suspensions it will be appreciated that with two opposed electromagnets these can be energised alternately to produce the desired first and second applications of magnetic fields and with suitable timing it may be possible to keep the particles suspended in the centre of the chamber.

The invention also provides, as a second aspect thereof, apparatus to separate superparamagnetic particles from a suspension thereof in a first fluid and re-suspending said particles in the same or another fluid, said apparatus comprising a container having a surface or zone towards which said particles may be drawn by a first application of a magnetic field, and from which surface or zone said particles may be drawn into re-suspension by a second application of a magnetic field and means for producing said first and second applications of magnetic fields.

The container normally has an inlet port and an outlet port and is advantageously made of transparent material or at least has a transparent "window" to permit illumination of the interior. If desired, means may be provided for projecting light into the container through such a window. The means for producing the first and second applications of magnetic fields preferably comprise two, spaced electromagnets.

The apparatus can readily form part of a small, inexpensive portable analyser which will be described below.

It is preferred that the superparamagnetic particles are also monodisperse beads. An example of how to produce monodisperse bead is given in EP 106873 (Sintef). The term "monodisperse" used herein is intended to encompass size dispersions having a diameter standard deviation of less than 5%. Advantageously, the beads are in the size range 1 to 10 microns, in particular the size range 3 to 6 microns, e.g. about 4.5 microns.

In order that the superparamagnetic particles can be used for the immobilisation or isolation of substrates, for example proteins, nucleic acids or cells, a suitable ligand is applied to the particles. Such ligands include, inter alia lectins, antibodies and single stranded nucleic acids. The ligands may be adsorbed onto the surface of each particle although it is preferred that they are bound in some way, such as by covalent linking to functionalised groups on the particles.

It is surprising that ligands carried by superparamagnetic monodisperse particles in the size range mentioned above react virtually as rapidly as if free in solution. By using monodisperse particles the reaction rate of ligand binding (or other reactions at or near the particle surface) and other parameters are particularly uniform. By using superparamagnetic particles one avoids magnetic aggregation or clumping of the particles during reaction, thus again ensuring uniform and rapid reaction kinetics.

The invention will find particular utility in cell separation. The relatively low shear produced on re-suspension of the particles is advantageous when viable cells are sought. The lack of clumping mentioned above means that unwanted matter, such as undesired cells, which may have become physically entrapped when the particles were drawn to the surface will be free in the re-suspension fluid and unlikely to be entrapped during subsequent washing steps.

In one embodiment of the invention the apparatus is combined with a particle counting device. This may comprise an array of charge coupled devices (CCDs) and imaging software as described in our co-pending International application PCT/EP 9002121 claiming priority from GB 8927742.0, filed 7 Dec. 1989. For example, a combined cell separator and particle counting device may be used to count cells of interest in a diverse population, e.g. a blood sample, and provide a valuable tool for diagnosis of disease. Briefly, magnetic beads coated with antibodies against the desired cell type are mixed with a sample and fed to a separation chamber according to the invention. The beads become attached to the desired cells which are then drawn to one side of the chamber by a first magnetic field produced by a first electromagnet. Unwanted sample is then flushed from the chamber and the beads bearing the desired cells are re-suspended in a washing buffer by the action of a second magnetic field produced by a second electromagnet. The washing step is repeated and the nuclei of the cells are then stained with a dye such as acridine orange. The beads are then drawn to the surface of the vessel by one of the magnetic fields and surplus dye is flushed from the chamber. The beads with cells attached are re-suspended by the action of the other electromagnet in a buffer containing detergent which leads to cell rupture and release of the stained nuclei. It is preferred to use stained nuclei rather than cells since nuclei tend not to exhibit such a wide size distribution as cells.

The stained nuclei are flushed from the separation chamber into a reading chamber. The reading chamber is illuminated with UV light from an appropriate source and the fluorescent light emitted by the stained nuclei passes through magnifying optics to produce an image on a CCD chip which comprises an array of charge coupled devices. An emittence filter is preferably present between the chamber and the CCD chip to select only light of the desired wavelength. It is possible to use a plurality of dyes which may selectively bind certain nuclei types in preference to others and use a plurality of suitable emittance filters in rotation such that the different nuclei types in the sample may be counted.

The invention also provides, as a third aspect thereof, apparatus for counting comprising apparatus according to the second aspect of the invention in combination with particle counter having an optical cell through which is passed a fluid containing particles to be counted, means for illuminating the particles in the optical cell and optical means for providing an image of the particles in an array of charge coupled devices such that the area of the image of each particle at the said array is approximately the same as the area of at least a single charge coupled device.

It will of course be apparent to the skilled person that the optical cell and separation chamber can be the same vessel.

As mentioned above, at least a part of the separation chamber is preferably transparent and it may be preferred to count whole cells separated from the original sample.

The term CCD array as used herein refers to an array of photosensitive CCDs which may for example, be of the frame-field or interline transfer type and may produce the required signals by current or voltage sensing. Such arrays are normally provided as integral CCD chips for use, for example, in solid state cameras and one commercially available CCD chip is that available from Phillips N. V.

It is desirable that the magnification is such that fluorescent light from a single nucleus will impinge on at least one CCD. Assuming that (i) a nucleus is generally circular in plan view and (ii) each CCD is substantially square then each nucleus is preferably magnified so that it substantially covers at least the area of a single a CCD and may partially cover the area of 2×2 or 3×3 array of CCDs. As the nuclei bearing fluid passes through the reading chamber the CCD chip is interrogated, preferably ten times so that a plurality of readings are taken for analysis. A plurality of readings for each sample is preferable since errors caused by overlap of the nuclei can be accounted for and size distribution of the nuclei can be calculated.

Figure 2:
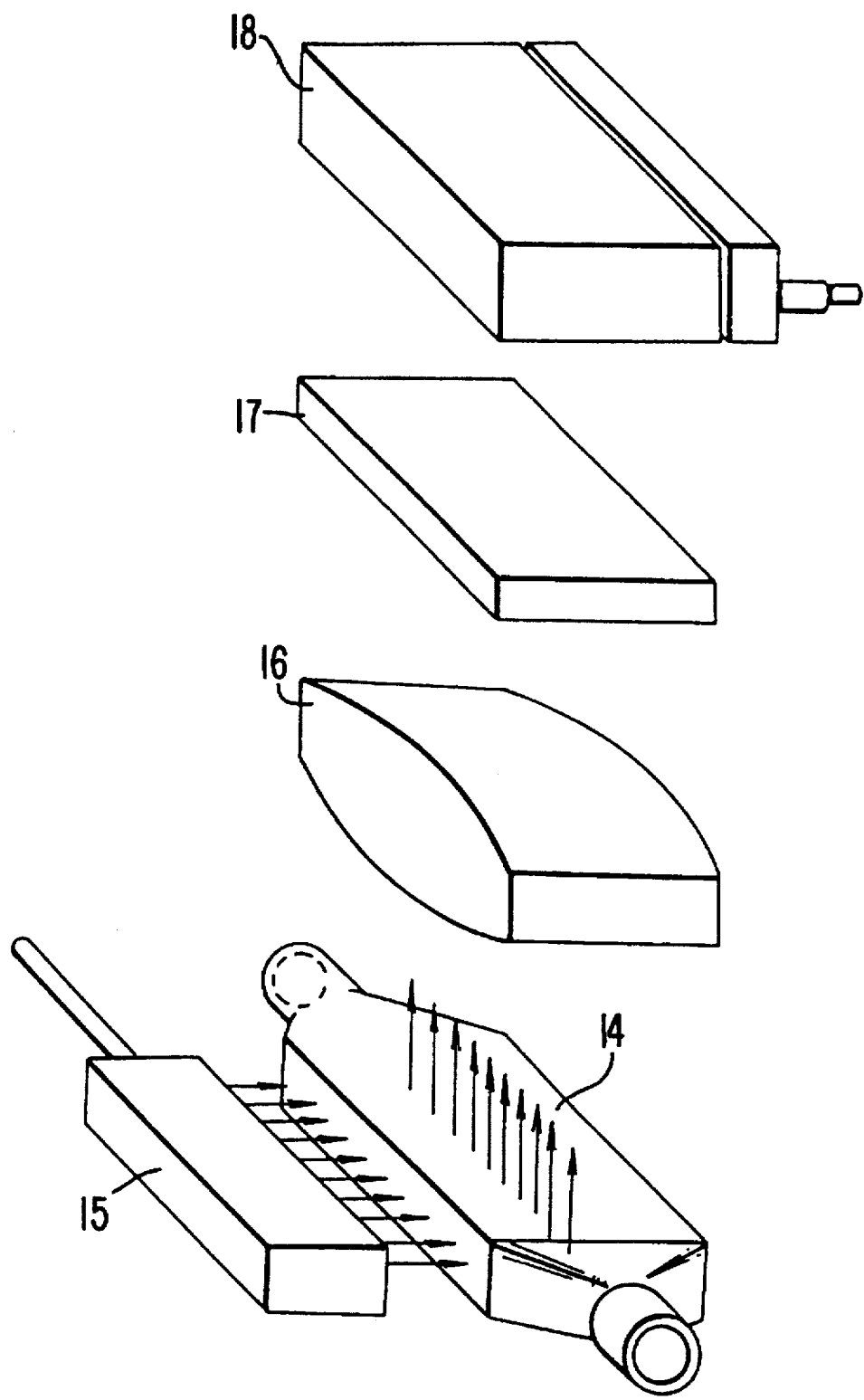

The invention will now be described by way of a non-limiting example with reference to the drawings in which:

FIG. 1 shows schematically an embodiment of apparatus according to the invention in conjunction with a plurality of conduits and receptacles; and FIG. 2 shows schematically a particle counting arrangement which can be combined with the apparatus shown in FIG. 1.

FIG. 1 shows a separation chamber 1 located between two spaced electromagnets 2,3. The separation chamber comprises an inlet port 4 and an outlet port 5. A common feed conduit 6 connects a plurality of receptacles 7–11 which are fed by a common pressure line 12 controlled by a pump, not shown, which maintains all the vessels at the same pressure. Outflow from each receptacle 7–11 is controlled by a respective pinch valve 13 (shown schematically as a arrow with an underscore). The volumes drawn off from the receptacles 7–11 thus depend only on the time of opening of a respective valve 13 and the rate of flow of the liquid (determined by the sizes of the connecting tubes and the viscosity of the liquid). Control of the valves 13 is automated by a computer as indicated below. All the tubing connecting the receptacles may be disposable to avoid contamination and/or clogging problems.

The outlet port 5 of the separation chamber 1 is connected to a reading chamber 14 shown diagrammatically in FIG. 2. To one side of the reading chamber 14 there is a UV light source 15 and above the chamber 14 are magnifying optics (represented schematically by a convergent lens 16), an emittence filter 17 and a CCD chip 18.

A combination of the apparatus shown in FIGS. 1 and 2 can be used as a cell counter. A cell bearing sample is mixed with superparamagnetic beads having a cell selective antibody coating thereon and placed in receptacle 7. Opening the respective valve 13 allows pressure from line 12 to force the sample and beads into the separation chamber 1 via the conduit 6. The chamber 1, which will have been prefilled with washing buffer, has a volume of about 2 ml; 100 μl of the sample may be transferred to the chamber. Energisation of one of the electromagnets for example electromagnet 2, aggregates the magnetic particles and selected cells to a zone 19 on the wall of the vessel 1 and the supernatant is then evacuated through outlet 5 using 3 ml of a wash solution (buffer) from receptacle 8. The magnetic particles and cells are then re-suspended by brief energisation of the other electromagnet, e.g. electromagnet 3, to apply a second magnetic field at a further zone 20 and if necessary the two electromagnets can be energised alternately to cause the particles to move within fresh washing buffer backwards and forwards across the chamber several times. The washing procedure is repeated at least once to ensure that no unwanted cells are trapped by the magnetic beads and attached cells. The magnetic particles and cells may then be aggregated by electromagnet 2 and the wash solution replaced by a staining solution, typically washing buffer containing acridine orange, from receptacle 9. After re-energisation of the electromagnets to re-suspend the particles the staining reaction is allowed to stain the cell nuclei. Magnetic re-aggregation may then be followed by replacement of the staining reagent by 3 ml of a wash solution containing a detergent taken from receptacle 10. Energisation of one of the electromagnets 2 or 3 causes the magnetic particles and cells to move across the chamber 1 and contact with the detergent causes the cells to rupture, whereupon the nuclei are released into the buffer. One electromagnet, is then energised to aggregate the magnetic particles and all residues attached thereto; the buffer containing the stained nuclei is then flushed through with further washing buffer into the reading cell 14 (shown in FIG. 2). Finally, the system may be cleaned out by drawing cleaning fluid from receptacle 11 through the chamber 1, e.g. 5 ml of a suitable washing buffer. The sample inlet may be backwashed with 2 ml buffer by using suitable valve arrangements. It should be noted here that either electromagnet 2 or electromagnet 3 may be used for aggregation of the magnetic particles; the other electromagnet being used re-suspend the particles.

The reading cell 14 is made from optical quality glass or plastics. The shape of the cell is designed to fit the optical lens system 16 and the CCD chip 18. The lens system 16 has a magnification ratio that will make a normal particle (e.g. a nucleus) trigger 3×3=9 CCDs in the CCD chip. By choosing this ratio, the analyzer faciliates measurements of both smaller and larger particles than normal. The CCD 18 chip is chosen on the basis of its CCD density, sensitivity and reaction time.

Since the fluorescent dye, e.g. acridine orange, has a definite wavelength for its emission, a filter 17 is placed between the lens system 16 and the CCD chip 18 to filter out light of other wavelengths.

The CCD chip 18 gives continuous information regarding what is happening in its viewing field. This information is transmitted to the processing unit in the analyzer (not shown).

The analyzer includes a computer (not shown) which handles all communication with the operator and all data analysis. Communication with the operator is via a conventional touch sensitive panel, such as a keyboard, and an LCD screen (neither of which are shown). At the beginning of the analysis the computer will tell the operator to check certain functions and how to insert the sample. The processor will control the valve function and monitor the pressure in the fluid system. The energisation of the magnetic fields is controlled and the data from the CCD chip 18 is collected.

The information from the CCD chim may, for example, be sampled as 10 "frame freeze pictures", because the information from the CCD chip will be real time information from a moving fluid. The information from the 10 pictures will be processed by commercially available imaging software. This software is capable of identifying the number of illuminated objects and the size distribution.

The data obtained from the 10 pictures is treated statistically and the results for the test are calculated.

The results of the analysis are presented on the LCD screen in terms of the number of cells and a histogram of the size distribution although other presentations will be apparent to the skilled person. Size distribution, for example, will give the operator a chance to see if the sample contained so many abnormal cells that further study is necessary.

A printer, e.g. a thermal printer, may be provided to print out a hard copy of the test results.

We claim:

1. A method of separating superparamagnetic particles from a suspension thereof in a first fluid and re-suspending said particles in the same or another fluid whereby said suspension in a container is subjected to a first application of a magnetic field to draw substantially all of said particles to a surface or zone of said container to form an aggregate, removing said first application of a magnetic field from said container, and subsequently re-suspending said particles in the same or another fluid within said container by a second application of a magnetic field at a different location relative to the said surface or zone.

2. A method of separating superparamagnetic particles as claimed in claim 1 wherein the first and second applications of a magnetic field are provided by electromagnet means.

3. A method of separating superparamagnetic particles from a suspension thereof in a first fluid and re-suspending said particles in the same or another fluid whereby said suspension in a container is subjected to a first application of a magnetic field to draw substantially all of said particles to a surface or zone of said container to form an aggregate and subsequently said aggregated particles which are in said aggregate are re-suspended in the same or another fluid within said container by a second application of a magnetic field at a different location relative to the said surface or zone to draw the particles into said fluid, wherein the first and second applications of a magnetic field are provided by electromagnet means comprising two spaced electromagnets to generate first and second magnetic fields.

4. Apparatus to separate super-paramagnetic particles from a suspension thereof in a first fluid and re-suspend said particles in the same or another fluid, said apparatus comprising:

a device for creating a first application of a magnetic field, removing said first application of said magnetic field, then creating a second application of a magnetic field;

a rod-free container having a peripheral interior surface including a portion towards which substantially all of said particles are drawn by said first application of a magnetic field to form an aggregate, and from said portion said particles which are in said aggregate are drawn to re-suspension in said same or another fluid by said second application of a magnetic field at a location relative to said portion different from said first application of a magnetic field to move said particles in a direction away from said portion and towards a central interior space of said container that is radially inwardly spaced from said peripheral interior surface so as to efficiently contact said same or another fluid;

wherein said device applies said first application of a magnetic field with a first electromagnet at a first position relative to said container and applies said second application of a magnetic field with a second electromagnet located at a second position relative to said container; and wherein said first electromagnet and said second electromagnet are fixed in relation to said container.

5. Apparatus to separate superparamagnetic particles as claimed in claim 4 in which the container has an inlet port and an outlet port.

6. An apparatus as claimed in claim 4, further comprising:

a particle counter in communication with said container to receive one of said first fluid and said another fluid, said particle counter having an optical cell through which said one of said first fluid and said another fluid is passed;

means for illuminating said particles in the optical cell; and optical means for providing an image of said particles on an array of charge coupled devices such that the area of the image of each of said particles at said array is approximately the same as an area of at least a single charge coupled device.

7. An apparatus as claimed in claim 4, wherein said means for illuminating said particles provides radiation approximately perpendicular to a light path from said optical cell to said array of charged coupled devices.

8. An apparatus as claimed in claim 4, further comprising at least one transmittance filter disposed between said optical cell and said array of charged coupled devices.

9. An apparatus as claimed in claim 4, further comprising means for processing signals from ones of said individual charge coupled devices to provide information concerning at least the number of said particles passing through the optical cell.

10. An apparatus as claimed in claim 6, wherein said container comprises said optical cell with a portion thereof being transparent.

11. An apparatus comprising:

a container including a peripheral interior surface;

a suspension in a first fluid including superparamagnetic particles; and a device that applies a first magnetic field to said container to cause substantially all of said particles to be drawn to a portion of said peripheral interior surface from said suspension in said first fluid to form an aggregate and applies a second magnetic field to said container to cause said particles to be drawn out in a direction away from said portion and towards a central interior space of said container that is radially inwardly spaced from said peripheral interior surface and be re-suspended in said suspension in said first fluid or a suspension in another fluid;

wherein said device applies said first application of a magnetic field with a first electromagnet at a first position relative to said container and applies said second application of a magnetic field with a second electromagnet located at a second position relative to said container; and wherein said first electromagnet and said second electromagnet are fixed in regulation to said container.

12. Apparatus for separating superparamagnetic particles as claimed in claim 11, wherein said container includes an inlet port and an outlet port.

* * * * *